US011684553B2

(12) United States Patent
Hoffmann et al.

(10) Patent No.: US 11,684,553 B2
(45) Date of Patent: Jun. 27, 2023

(54) CURABLE COMPOSITION FOR DENTAL RETRACTION

(71) Applicant: 3M INNOVATIVE PROPERTIES COMPANY, St. Paul, MN (US)

(72) Inventors: Henning Hoffmann, Windach (DE); Peter Osswald, Tuerkheim (DE); Joachim Zech, Kaufering (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 628 days.

(21) Appl. No.: 16/477,702

(22) PCT Filed: Jan. 15, 2018

(86) PCT No.: PCT/US2018/013697
§ 371 (c)(1),
(2) Date: Jul. 12, 2019

(87) PCT Pub. No.: WO2018/136351
PCT Pub. Date: Jul. 26, 2018

(65) Prior Publication Data
US 2019/0358130 A1 Nov. 28, 2019

(30) Foreign Application Priority Data
Jan. 18, 2017 (EP) ..................... 17151922

(51) Int. Cl.
| A61K 6/18 | (2020.01) |
| A61C 9/00 | (2006.01) |
| C08L 51/08 | (2006.01) |
| C08L 83/04 | (2006.01) |
| A61K 6/90 | (2020.01) |
| A61K 6/19 | (2020.01) |

(52) U.S. Cl.
CPC .............. *A61K 6/18* (2020.01); *A61C 9/0033* (2013.01); *A61K 6/19* (2020.01); *A61K 6/90* (2020.01); *C08L 51/085* (2013.01); *C08L 83/04* (2013.01)

(58) Field of Classification Search
CPC ... A61K 6/18; A61K 6/90; A61K 6/19; A61C 9/0033; C08L 51/085; C08L 83/04
See application file for complete search history.

(56) References Cited

U.S. PATENT DOCUMENTS

| 3,242,218 A | 3/1966 | Miller |
| 3,715,334 A | 2/1973 | Karstedt |
| 3,775,352 A | 11/1973 | Leonard |
| 3,814,730 A | 6/1974 | Karstedt |
| 3,933,880 A | 1/1976 | Bergstrom |
| 4,035,453 A | 7/1977 | Hittmair |
| 4,273,902 A | 6/1981 | Tomioka |
| 4,468,202 A | 8/1984 | Cohen |
| 4,657,959 A | 4/1987 | Bryan |
| 4,782,101 A | 11/1988 | Waller |
| 5,159,096 A | 10/1992 | Austin |
| 5,249,862 A | 10/1993 | Herold |
| 5,286,105 A | 2/1994 | Herold |
| 5,362,495 A | 11/1994 | Lesage |
| 5,464,131 A | 11/1995 | Keller |
| 5,684,060 A | 11/1997 | Konings |
| 5,750,589 A | 5/1998 | Zech |
| 5,863,965 A | 1/1999 | Hare |
| 7,572,842 B2 | 8/2009 | Zech |
| 7,732,508 B2 | 6/2010 | Zech |
| 2002/0147275 A1 | 10/2002 | Bublewitz |
| 2004/0124396 A1 | 7/2004 | Flynn |
| 2005/0027032 A1 | 2/2005 | Hare |
| 2005/0239958 A1 | 10/2005 | Bublewitz |
| 2008/0200584 A1 | 8/2008 | Bottcher |
| 2010/0035213 A1 | 2/2010 | Lubbers |
| 2010/0248190 A1 | 9/2010 | Chen |
| 2011/0046262 A1 | 2/2011 | Bublewitz |
| 2012/0077142 A1 | 3/2012 | Maurer |
| 2012/0295222 A1 | 11/2012 | Lesage |
| 2013/0273495 A1 | 10/2013 | Dragan |

(Continued)

FOREIGN PATENT DOCUMENTS

| DE | 4427528 | 2/1996 |
| EP | 0231420 | 8/1987 |

(Continued)

OTHER PUBLICATIONS

Kugel, "Investigation of a New Approach to Measuring Contact Angles for Hydrophilic Impression Materials", Journal of Prosthodontics, Mar.-Apr. 2007, vol. 16, No. 02, pp. 84-92.

(Continued)

*Primary Examiner* — Patrick D Niland
(74) *Attorney, Agent, or Firm* — 3M Innovative Properties Company

(57) ABSTRACT

The invention relates to a curable composition for dental retraction comprising a resin matrix comprising at least one polyorganosiloxane with at least two olefinically unsaturated groups as component A1, at least one organohydrogenpolysiloxane as component A2, optionally at least one vinyl functional QM silicone component as component A3, at least one alkylsiloxane having at least one carbinol, silanol, or alkoxy moiety as component B, optionally surfactant(s) as component E, optionally additive(s) as component F, a filler system comprising filler(s) as component D, a catalyst system comprising addition cure catalyst component C-A suitable to cure components A1 and A2, condensation cure catalyst component C-B suitable to cure component B, the curable composition being provided as a kit of part comprising a Catalyst Part I and a Base Part II the Catalyst Part I comprising components C-A, C-B, A1, the Base Part II comprising components A2, A1, B, wherein each of components D, E and F and A3, if present, can be present either in the Catalyst Part I or the Base Part II or the Catalyst Part I and the Base Part II, and wherein component B is present in an amount of 6 wt. % or more with respect to the whole composition.

20 Claims, 1 Drawing Sheet

(56) References Cited

U.S. PATENT DOCUMENTS

2014/0170596 A1 6/2014 Angeletakis
2014/0348921 A1 11/2014 Lesage

FOREIGN PATENT DOCUMENTS

| EP | 0480238 | 4/1992 |
|---|---|---|
| EP | 0639622 | 2/1995 |
| EP | 0730913 | 9/1996 |
| EP | 1776080 | 4/2007 |
| EP | 2231102 | 9/2010 |
| WO | WO 1997-003110 | 1/1997 |
| WO | WO 2005-013925 | 2/2005 |
| WO | WO 2007-001869 | 1/2007 |
| WO | WO 2010-138433 | 12/2010 |
| WO | Wo 2012-177985 | 12/2012 |
| WO | WO 2016-196048 | 12/2016 |

OTHER PUBLICATIONS

Osswald, "Retraction Capability of Different Types of Materials—IADR Abstract Archive", AADR/CADR Annual Meeting, Los Angeles, California—Presentation ID 1124, Mar. 2016, 2 pages.

Shih, "Synthesis and Characterization of Polycarbonate/ Polydimethylsiloxane Multiblock Copolymer Prepared from Dimenthylsiloxane and Various Aromatic Dihydroxyl Monomers", Journal of Applied Polymer Science, Jan. 2000, vol. 75, No. 04, pp. 545-552.

International Search Report for PCT International Application No. PCT/US2018/013697, dated Apr. 9, 2018, 5 pages.

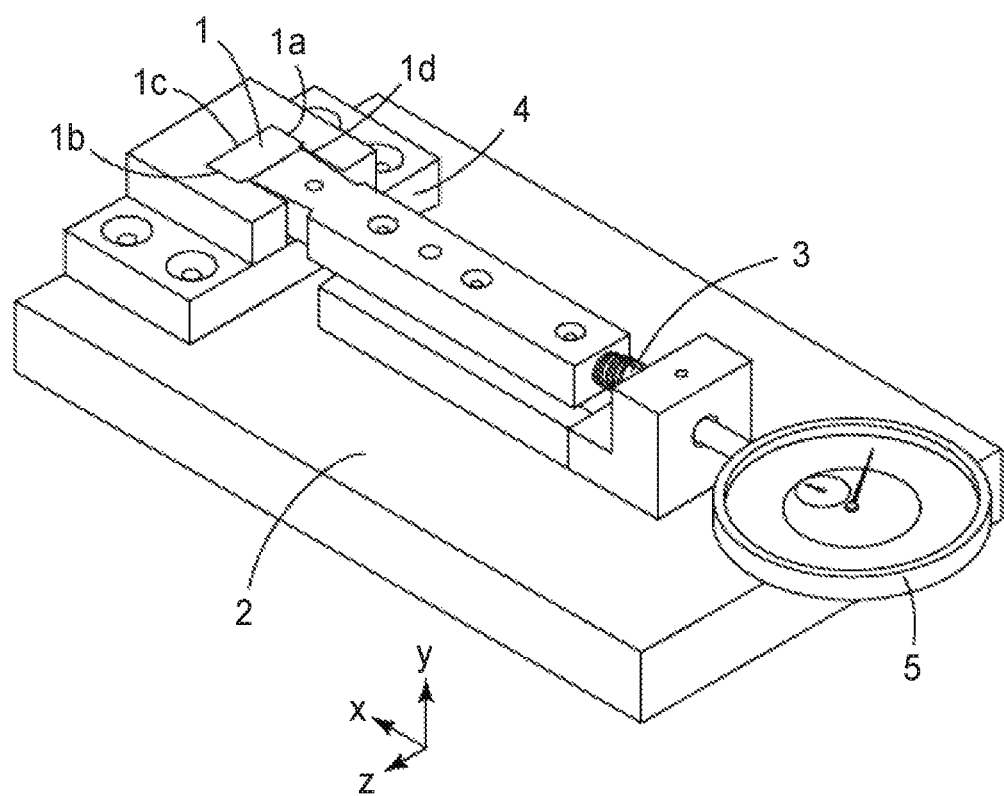

CURABLE COMPOSITION FOR DENTAL RETRACTION

CROSS REFERENCE TO RELATED APPLICATIONS

This application is a national stage filing under 35 U.S.C. 371 of PCT/US2018/013697, filed Jan. 15, 2018, which claims the benefit of EP Application No. 17151922.6, filed Jan. 18, 2017, the disclosures of each of which are incorporated by reference herein in their entireties.

FIELD OF THE INVENTION

The invention relates to a curable composition for dental use, in particular for use as dental retraction material. The curable composition comprises a resin matrix, a filler system and a catalyst system, wherein the catalyst system comprises two different kinds of catalysts.

BACKGROUND ART

For producing an accurate dental restoration it is typically important to have the margin of the preparation of the teeth clearly visible in a dental impression. Therefore, it is often recommended to widen the sulcus in a retraction process. This is typically done by using a retraction cord or a retraction paste before the dental impression step is conducted.

This retraction step is an additional, often time consuming and sometimes difficult step to perform for the dental practitioner.

A good retraction material has the ability to keep the sulcus of a tooth open and withstand the forces of the surrounding soft dental tissue. In this respect, often pastes having a high viscosity are suggested.

However, a material having a high viscosity is not suitable as dental impression material, as this material is typically not able to reproduce the fine contours (precision) on the teeth surface, a property needed for producing an accurate dental restoration.

Technical solutions known today typically require separate pastes or materials for conducting either the dental retraction or dental impression process.

Known are compositions which increase the viscosity upon mixture by combining two setting mechanisms.

US 2005/239958 A1 (Bublewitz et al.) describes a two-step curable mixer-suitable material for making dental impressions. The system contains at least one compound having at least two alkenyl groups, at least one organohydrogenpolysiloxane, at least one hydrosilylation catalyst, wherein at least one polymeric compound having at least one alkynyl group, at least one compound having at least one Si—OR structural unit and at least one condensation catalyst is contained.

U.S. Pat. No. 7,732,508 (Zech et al.) relates to an automixable putty impression material. The composition comprises at least one polydiorganoxiloxane having at least two aliphatically unsaturated groups, at least one organohydrogenpolysiloxane, at least one alkylsiloxane having at least one carbinol, carboxy or amino group, at least one condensation cure compound and at least one addition cure precious metal catalyst.

US 2008/0200584 A1 (Bottcher et al.) describes a silicone impression material with two-stage curing mechanism. The impression material comprises at least one compound (a) with at least two alkenyl groups, at least one compound (b) with at least one chelating group, at least one organohydropolysiloxane (c), at least one hydrosilylation catalyst (d) and at least one compound with a chelatable metal component (e), the chelating group exhibiting no reactive groups which can react with component (c) and/or component (d).

EP 1 776 080 B1 (Dentsply) is directed to a method of taking a dental impression of a dentition including sub-gingival parts, comprising the steps of (i) conditioning the dentition including sub-gingival parts by application thereto of a wetting agent comprising a surfactant and a carrier; (ii) contacting the dentition with a dental impression material selected from hydrophilic and hydrophobic dental impression materials, whereby the impression material is allowed to flow into sub-gingival parts, further comprising the step of preparing the dentition with a gingival retraction cord, wherein said gingival retraction cord has been contacted with a wetting agent further comprising a haemostatic agent.

US 2002/0147275 (Bublewitz et al.) relates to a multi-component system for making impressions comprising components A and B, wherein component A contains a) at least one compound having at least two alkenyl groups, b) at least one compound having at least one alkynyl group and/or at least one compound having at least one Si—OH structural unit, and c) at least one organohydrogenpolysiloxane, and component B contains d) at least one condensation catalyst and/or condensation cross-linking agent and e) at least one hydrosilylation catalyst. In Example 6 a formulation is described obtained by mixing two components in a ratio of 1 to 5. The content of component b) in that formulation is about 5 wt. % with respect to the whole composition. Known are also references dealing with dental retraction pastes.

US 2014/0170596 A1 (Angeletakis) describes a two part retraction system than be inserted into the sulcus to form a semi-rigid porous elastomer releasing a hemostatic agent suitable for sulcus retraction such that a dental impression may be completed by a dental practitioner.

US 2010/0035213 A1 (Lubbers et al.) describes a dental kit and method for retracting sulcus. The method comprises the steps of (i) molding a dental impression of a portion of the patients mouth with a curable composition, (ii) removing the cured mold, (iii) applying an expanding silicone material with expands during curing to the adjacent area between the tooth and gingiva and (iv) reapplying the mold to the mouth of the patient to form a barrier to the expansion of the silicone material to limit the expansion of the silicon only in the direction toward the sulcus.

As some of the compositions described in the prior art are often formulated as dental impression materials and are intended to be mixed by using automated dosing and mixing systems (e.g. Pentamix™ device; 3M Oral Care), the mixing ratio of the respective base and catalyst pastes is typically 5:1 with respect to volume.

However, such a mixing ratio is typically not suitable for dental retraction purposes, where only a small amount of material is needed and where the material needs to be dispensed through thin cannulas or nozzles.

DESCRIPTION OF THE INVENTION

According to one aspect there is a desire for a curable composition, which can be used as dental retraction material having the following properties:

The composition has sufficient capability to keep the sulcus of a tooth open.

The composition is easy to mix and easy to apply to the sulcus of a tooth.

Ideally, it should be possible to mix the respective pastes by using a static mixing tip having a nozzle allowing the application of the mixed composition into the sulcus of a tooth.

According to a further aspect, there is a desired for a curable composition which, after curing, has sufficient strength to allow the easy removal of the cured composition from the sulcus of a tooth.

One or more of the above objects are addressed by the curable composition described in the present text and claims.

In one embodiment, the invention features a curable composition for dental retraction comprising:
a curable composition for dental retraction comprising:
  a resin matrix comprising:
    at least one polyorganosiloxane with at least two olefinically unsaturated groups as component A1,
    at least one organohydrogenpolysiloxane as component A2,
    optionally at least one vinyl functional QM silicone component as component A3,
    at least one alkylsiloxane having at least one carbinol, silanol or alkoxy moiety as component B,
    optionally surfactant(s) as component E,
    optionally additive(s) as component F,
  a filler system comprising filler(s) as component D,
  a catalyst system comprising:
    catalyst component C-A/addition cure catalyst suitable to cure components A1 and A2,
    catalyst component C-B/condensation cure catalyst suitable to cure component B, the curable composition being provided as a kit of part comprising a Catalyst Part I and a Base Part II
    the Catalyst Part I comprising components C-A, C-B, A1,
    the Base Part II comprising components A2, A1, B,
  wherein each of components D, E and F can be present either in the Catalyst Part I or the Base Part II or the Catalyst Part I and the Base Part II,
  wherein component B is present in an amount of 6 wt. % or more with respect to the whole composition.

Described is also a process of producing the curable composition as described in the present text.

Described is also a packaging system containing the components of the composition described in the present text.

The invention also relates to a kit of parts comprising the curable composition as described in the present text and either of the following components alone or in combination:
  Dental impression material;
  Retraction caps;
  Application device;
  Impression Trays.

Moreover, the invention also features the composition described in the present text for use in a process comprising the steps of
  mixing the compositions of the Catalyst Part and the Base Part of the curable composition described in the present text,
  applying the obtained mixture into the sulcus of a tooth (e.g. in an amount of 5 to 500 µl),
  letting the composition cure,
  removing the cured composition from the sulcus.

Further, the invention is directed to the use of an alkylsiloxane having at least one carbinol, silanol or alkoxy moiety as described in the present text for enhancing the consistency of a curable composition as described in the present text.

Unless defined differently, for this description the following terms shall have the given meaning:

A "dental composition" or a "composition for dental use" or a "composition to be used in the dental field" is any composition which can be used in the dental field. In this respect, the composition should not be detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "putty like dental impression material" is a kneadable dental impression material having a consistency of 35 mm or below according to ISO 4823.

A "dental retraction material" or a "composition for dental retraction" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

"Dental situation" means a part or all of a person's dentition and surrounding structures in the oral cavity, including subgingival portions.

"Dental tissue" means the hard and soft dental tissue. Hard dental tissue comprises the tissue of dental tooth (including dentin and enamel). Soft dental tissue comprises the tissue surrounding the hard dental tissue, i.e. the gum.

The term "compound" or "component" is a chemical substance which has a particular molecular identity or is made of a mixture of such substances, e.g., polymeric substances.

A "liquid" is any solvent or liquid which is able to at least partially disperse, dissolve or suspend the components being present in the composition described in the present text at ambient conditions (e.g. 23° C.). By "paste" is meant a soft, viscous mass of solids (i.e. particles) dispersed in a liquid.

A "particle" or "particulate filler" means a substance being a solid having a shape which can be geometrically determined. The shape can be regular or irregular. Particles can typically be analysed with respect to e.g. grain size and grain size distribution. A particulate filler is composed of free-flowing particles.

"Room temperature hardening or curing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is inhibited) at room temperature.

The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound. A "silicone elastomer" is an elastomeric polymer comprising silicone units, i.e. comprising the elements Si, O, C and H, in particular dimethylsiloxane (—O—Si(CH$_3$)$_2$—) units.

"Elastomeric" means rubber-elastic or rubber-like. Elastomeric materials can be characterized e.g. by a certain tensile or tear strength and/or elongation at break. Other means for characterizing elastomeric materials include the measurement e.g. of the Young's modulus. Elastomeric materials typically have an E-modulus in the range from 0.8 to 10 MPa or from 1 to 8 MPa or from 1.5 to 6 MPa (determined e.g. according to DIN 53504, thickness of sample: 2 mm).

"Poly" means that the respective substance contains at least 10 repeating units of a certain monomer moiety.

The term "hydrosilation" means the addition of a compound comprising SiH-groups to a compound containing an aliphatic multiple bond (e.g., an olefinically or acetylenic unsaturation), preferably a vinyl group, —CH=CH$_2$.

The terms "vulcanizing, hardening, crosslinking, setting, curing" are used interchangeable and refer to silicones that have as a common attribute the development of a crosslinked elastomer from relatively low molecular weight linear or branched polymers by means of a chemical reaction that simultaneously forms these crosslinks and effectively extends chain length at room temperature.

"Surfactant" or "Hydrophilating agents" are agents that are able to either lower the surface tension of water, if used alone (like surfactants), or contribute to a lower surface tension, if used in combination with a surfactant (sometimes referred to as wetting-enabler). If desired, the effect of lowering the surface tension of water can be measured by determining the water-contact angle as described in more detail below.

The term "automixer-suitable material" relates to a multi-component material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™", "Pentamix™ 2" and "Pentamix™ 3" devices of 3M ESPE Company (cf. U.S. Pat. Nos. 5,286,105 and 5,249,862).

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not willfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The term "comprise" shall include also the terms "consist essentially of" and "consists of".

BRIEF DESCRIPTION OF FIGURES

FIG. 1 shows a device which can be used for determining the rheological properties of the curable composition (e.g. flowing properties of the composition under a predefined load if placed in a predefined mould).

DETAILED DESCRIPTION OF THE INVENTION

It has been found that the composition described in the present text is advantageous in various aspects.

The composition is well suited to be used for retracting soft dental tissue from hard dental tissue.

As outlined above, a dental retraction composition needs to be inserted into the sulcus of a tooth. This is typically done by using a cannula or nozzle having a small diameter.

The composition described in the present text and obtained shortly after combining the components contained in the catalyst part and the base part has a sufficiently low viscosity to allow an easy mixing on the one hand and an easy application of the mixed composition into the sulcus of a tooth on the other hand.

The composition described in the present text can also be formulated in a convenient mixing ratio of the base part and the catalyst part from 4:1 to 1:1 with respect to volume.

Further, after mixing the components of the curable composition, the obtained composition has a consistency which is sufficiently high to keep the sulcus of a tooth open. Thus, once applied into the sulcus of a tooth, the composition remains in the sulcus and is not expelled from the sulcus due to the pressure exerted by the surrounding tissue.

Moreover, after hardening the composition has a sufficient strength which allows an easy removal of the composition from the sulcus, preferably in one piece, if desired.

If desired, the composition described in the present text can typically be characterized by one or more, sometimes all of the following parameters:

curing time: within 10 min at 23° C.;

Shore hardness A: from 25 to 80 determined according to DIN ISO 7619-1:2012-02;

tensile strength: from 1.0 to 10 determined according to DIN 53504:2009-10;

consistency of composition of the Catalyst Part and/or the Base Part being from 25 to 50 mm, if determined according to ISO 4823:2015;

water contact angle of composition of the Catalyst Part and/or the Base Part measured 10 s after placing a drop of water onto the surface of the composition: <90';

residual gap resistance: at least 2.0 mm or at least 2.2 mm.

In certain embodiments, the combination of the following features is sometimes desirable: tensile strength and residual gap resistance.

If desired, the respective parameters can be determined as outlined in the example section.

The composition described in the present text comprises a resin matrix, a filler system and a catalyst system, wherein the composition is provided as a kit of parts comprising a catalyst part or paste and a base part or paste.

The curable composition comprises polyorganosiloxane(s) with at least two olefinically unsaturated groups as component A1.

The nature and structure of component A1 is not particularly limited unless the desired result cannot be achieved. The hardening of component A1 is effected by a polyaddition reaction.

This curing mechanism is typically based upon the polyaddition of silanes with aliphatically unsaturated double bonds (e.g. vinyl groups) in the presence of a catalyst, such as Pt containing compound. The respective compositions are often referred to as VPS materials and the curing mechanism as hydrosilation.

The organopolysiloxane is a molecule in which at least two organic groups are groups with an ethylenically unsaturated double bond. Generally, the groups with an ethylenically unsaturated double bond can be located on any monomeric unit of the organopolysiloxane. It can, however, be preferred, that the groups with an ethylenically unsaturated double bond are located on or at least near the terminal monomeric units of the polymer chain of the organopolysiloxane. In another embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this structure are represented by the following formula (I):

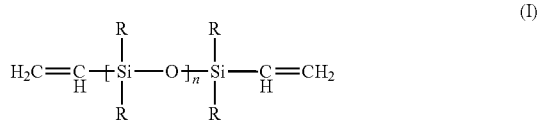

(I)

in which the radicals R, independently from each other, represent a non-substituted or substituted, monovalent hydrocarbon group with 1 to 6 C atoms, which is preferably free from aliphatic multiple bonds and where n generally can be chosen such that the viscosity of the organopolysiloxanes lies between 4 and 1,000,000 mPa*s or between 6 and 500,000 or between 10 and 100,000 mPa*s (23° C.). The parameter n can, e.g., be in the range of 10 to 10,000.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment, at least about 50% of the radicals R are methyl groups. Examples of other radicals R that can be present in the organopolysiloxanes according to the above formula are ethyl, propyl, isopropyl, n-butyl, tert.butyl, the pentyl isomers, the hexyl isomers, vinyl, propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is included herein by reference.

Particularly preferred are linear polydimethylsiloxanes according to the above formula having viscosities within the specified viscosity ranges and end groups comprising dimethylvinylsiloxy units and methyl groups as the radicals R.

A component A1 which can be employed can consist of one type (a1) of organopolysiloxane. The organopolysiloxane can have a viscosity starting in the range of 5 to 1,000,000 mPa*s, or 10 to 500,000 mPa*s or 20 to 50,000 or 30 to 40,000 mPa*s.

It is, however, also possible that component A1 comprises two or more constituents (a1), (a2) and so on, which can differ, e.g., in the chemical composition of their backbone, or their molecular weight, or their substituents or their viscosity, or any other differentiating feature or two or more of the above mentioned features.

In one embodiment the difference in viscosities of different constituents of component A1 can be higher than a factor of 2, e.g., higher than a factor of 5, higher than a factor of 10, higher than a factor of 20, higher than a factor of 30, higher than a factor of 40, higher than a factor of 50, higher than a factor of 60, higher than a factor of 70, higher than a factor of 80, higher than a factor of 90 or higher than a factor of 100. The difference in viscosities can be even higher, e.g., higher than a factor of 200, higher than a factor of 300, higher than a factor of 500, higher than a factor of 800, higher than a factor of 1,000 or higher than a factor of 5,000, it should, however, preferably not exceed a value higher than a factor of 10,000. It should be kept in mind that the values mentioned above relate to a factor for the difference in viscosities, not the viscosity values themselves.

If component A1 contains constituents of different viscosities, the ratio of the amount of constituent with the lowest viscosity to the amount of constituent with the highest viscosity can be chosen relatively freely, depending on the desired properties of the precursors and the cured resin. It can, however, be advantageous when the ratio of the amount of constituent with the lowest viscosity to the amount of constituent with the highest viscosity is within a range of from 1:20 to 20:1, especially 1:10 to 10:1 or 1:5 to 5:1. Good results can e.g. be obtained with ratios of from 1:3 to 3:1 or 1:2 to 2:1. It can furthermore be adequate in some cases, when the amount of constituent with the highest viscosity is about equal to or higher than the amount of constituent with the lowest viscosity, resulting in a value of from 0.9:1 to 3:1 for the ratio of the amount of constituent with the highest viscosity to the amount of constituent with the lowest viscosity. All of the ratios are based on the weight of the constituents.

Component A1 is typically present in the following amounts:
Lower limit: at least 0.1 or at least 1 or at least 3 wt. %;
Upper limit: utmost 45 or utmost 40 or utmost 35 wt. %;
Range: from 0.1 to 45 or from 1 to 40 or from 3 to 35 wt. %;
wt. % with respect to the weight of the whole composition.

The curable composition also comprises organohydrogenpolysiloxanes(s) as component A2.

The nature and structure of component A2 is not particularly limited unless the desired result cannot be achieved.

Component A2 acts as a crosslinker capable of crosslinking component A1.

Component A2 is typically an organohydrogenpolysiloxane with at least 3 SiH groups per molecule.

An organohydrogenpolysiloxane typically contains from about 0.01 to about 1.7 wt. % silicon-bonded hydrogen or from 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least 50%, preferably 100%, of the hydrocarbon radicals R that are bonded to silicon atoms are methyl radicals.

Organohydrogenpolysiloxanes which can be suitable include those having a viscosity of 10 to 1,000 mPa*s or from 15 to 550 mPa*s or from 20 to 250 mPa*s (at 23° C.).

Component A2 can be present in the following amounts:
Lower limit: at least 0.1 or at least 1 wt. %;
Upper limit: utmost 20 or utmost 15 wt. %;
Range: from 0.1 to 20 or from 1 to 15 wt. %;
wt. % with respect to the weight of the whole composition.

According to one embodiment the curable composition may also comprise vinyl functional QM silicone component(s) as component A3.

Vinyl functional QM silicone component(s) comprise as Q a quadrifunctional $SiO_{4/2}$ unit and as M building blocks such as monofunctional units $R_3SiO_{1/2}$, wherein R is vinyl, methyl, ethyl or phenyl or tri- or bi-functional units.

Examples of suitable vinyl functional QM silicone component(s) A3 include VQM 809, VQM 807, VQM 803, VQM 1603, VQM 806, VQM 881, VQM 885 and VQM 1773 (Evonik Hanse Company).

Examples of suitable vinyl functional QM silicone component(s) A3 are also described in e.g. US 2005/0027032. The content of this document with respect to the description of QM resins is herewith incorporated by reference.

Vinyl functional QM silicone component(s) A3 can be used in addition to the organopolysiloxanes described above.

Using vinyl functional QM silicone components may help to enhance the tensile strength of the cured composition. A sufficient tensile strength can be beneficial for removing the cured composition from the sulcus of a tooth in one piece.

Further, it was found that by adding vinyl functional QM silicone components to the composition the amount of plasticizers like mineral oil and/or Vaseline can be reduced.

If present, component A3 is present in the following amounts:
Lower limit: at least 0.1 or at least 1 or at least 3 wt. %;
Upper limit: utmost 65 or utmost 60 or utmost 55 wt. %;
Range: from 0.1 to 65 or from 1 to 60 or from 3 to 55 wt. %;
wt. % with respect to the weight of the whole composition.

The curable composition comprises also at least one alkylsiloxane having at least one carbinol, silanol, or alkoxy moiety as component B.

Component B is present in an amount of 6 wt. % or more with respect to the whole composition.

The nature and structure of component B is not particularly limited unless the desired result cannot be achieved.

Generally, as a component B all types of polyalkylsiloxanes having at least one carbinol, silanol, or alkoxy group or a mixture of two or more of such groups can be employed as components B.

Using polyalkylsiloxanes having at least one silanol or alkoxy group are sometimes preferred.

It is generally possible that the Catalyst Part, or the Base Part or the Catalyst Part and the Base Part contains component B, such as a polydiorganosiloxane having at least one carbinol, silanol or alkoxy group.

Polydiorganosiloxane having at least one silanol group contain the structural moiety Si—OH.

An example of a suitable polysiloxane having two or more hydroxy groups includes polydialkylsiloxanes, for example polydimethylsiloxane, that are terminated with a hydroxy group at both opposite ends of the polymer chain. Generally, the hydroxyl terminated polydialkylsiloxanes will have a weight average molecular weight of 900 to 500,000, for example between 1,500 and 150,000 g/mol.

Suitable silane compounds having two or more hydrolysable groups include in particular esters of silic acid, esters of polysilic acid and polysiloxanes having two or more alkoxy groups bound to a silicium atom. Typical examples include compounds according to the formula:

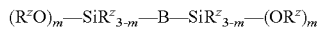

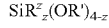

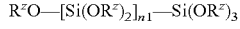

wherein B represents the divalent group of formula $O-(SiR_2-O)_{m2}-$ with R representing an aromatic or aliphatic hydrocarbon group (e.g. C1 to C12) which may optionally be substituted and m2 represents a value of 10 to 6000, R' and $R^z$ independently represents an alkyl group or an aryl group (e.g. C1 to C12) that may be substituted, n1 represents a value of 1 to 100, m is an integer of 1 to 3 and z is 0, 1 or 2.

In one embodiment component B contains at least one component of the formula:

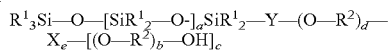 (II) or

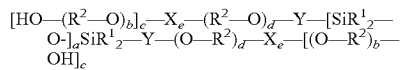 (III) or

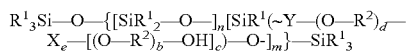 (IIIa) or (IIIb)

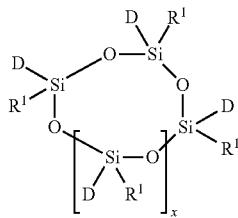

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or —Y—(O—$R^2)_d$—$X_e$—[(O—$R^2)_b$—OH]$_c$ with at least one residue —Y—(O—$R^2)_d$—$X_e$—[(O—$R^2)_b$—OH]$_c$ per molecule, 1≤a≤10.000, 0≤b≤500, 1≤c≤6, 0≤d≤500, e is 0 or 1, 0≤n≤500, 0≤m≤100 where m+n exceed 5 and x is 0, 1, 2, 3, 4, 5 or 6.

Preferred examples of component B include polydimethylsiloxanes with terminal or pendant carbinol groups.

The polydimethylsiloxanes are preferably linear but can also be cyclic or T-shaped.

A preferred structure is for example:

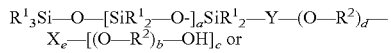 or

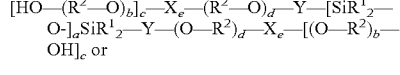 or

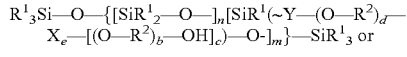 or

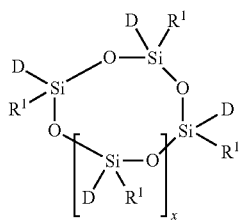

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or —Y—(O—$R^2)_d$—$X_e$—[(O—$R^2)_b$—OH]$_c$ with at least one residue —Y—(O—$R^2)_d$—$X_e$—[(O—$R^2)_b$—OH]$_c$ per molecule, 1≤a≤10.000, 0≤b≤500, 1≤c≤6, 0≤d≤500, e is 0 or 1, 0≤n≤500, 0≤m≤100 where m+n exceed 5 and x is 0, 1, 2, 3, 4, 5 or 6.

Also preferred are:

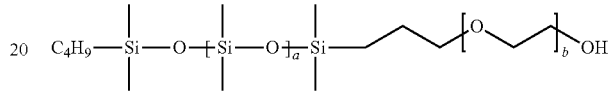

like MCR-C13 from Gelest company (CAS: 67674-67-3)

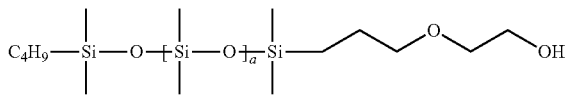

like MCR-C12 and MCR-C22 from Gelest company (CAS: 207308-30-3)

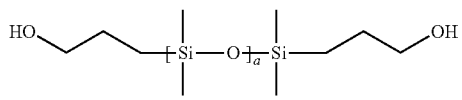

like Rhodorsil™ Oil 1647 V 60 and 1615 V 500 from Rhône-Poulenc (CAS: 58130-02-2)

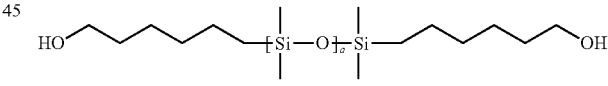

like Tegomer H-Si 2111, 2311 and 2711 from Th. Goldschmidt

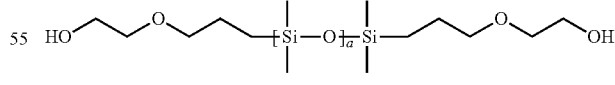

synthesized from allylglycol and Si—H terminated silicon oil

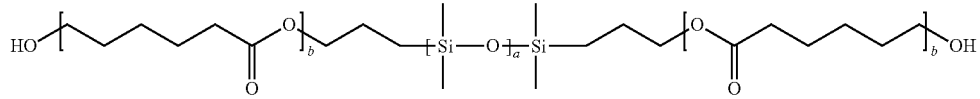

like DBL-C31 from Gelest company (CAS: 120359-07-1) or Tegomer H-Si 6440

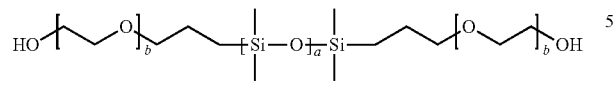

synthesized from allypolylglycol and Si—H terminated silicon oil according available from Hanse Chemie

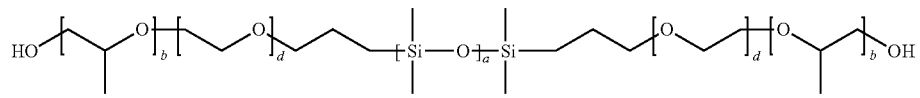

(EO+PO Adduct: Rhodorsil™ Oil 10646 from Rhône-Poulenc (CAS: 94469-32-6))

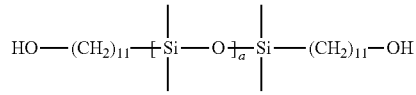

available from 10-undecene-1-ol and Si—H terminated silicon oil

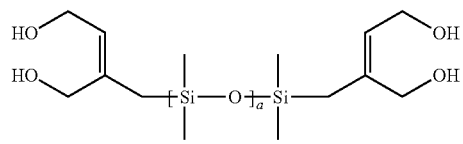

synthesized from 2-butin-1,4-diol and Si—H terminated silicon oil

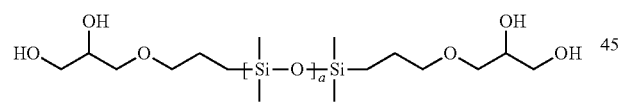

synthesized from allylglycerol and Si—H terminated silicon oil, or from DMS-E01, E12 or E21 from Gelest company (CAS: 104780-61-2)

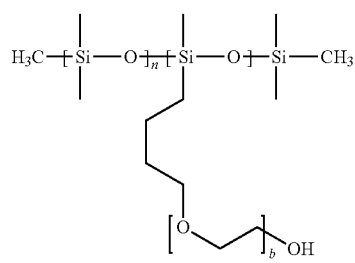

synthesized from Si—H pendant silicone oil and allyl polyglycole according to e.g. to U.S. Pat. No. 5,159,096,

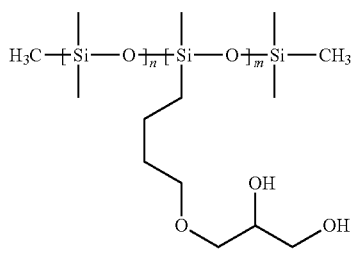

synthesized from Rhodorsil™ Oil 21620 from Rhône-Poulenc (CAS: 68440-71-1) and water

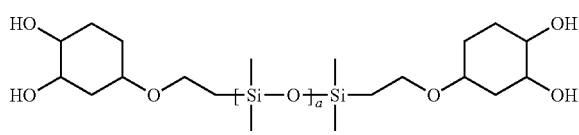

synthesized from VCHO and Si—H terminated silicon oil and addition of water

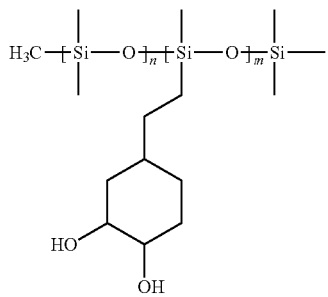

synthesized from Silicorelease Poly 200 or RCA 200 from Rhône-Poulenc (CAS: 67762-95-2) and water

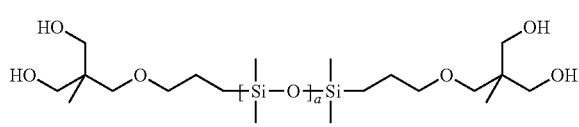

synthesized from trimethylolpropane-monoallyl ether and Si—H terminated silicon oil

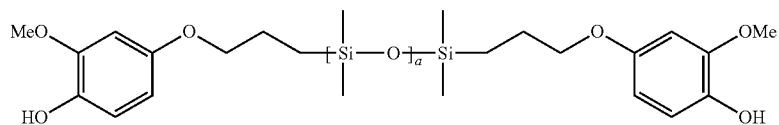

synthesized from eugenole and Si—H terminated silicon oil e.g. according to WO 97/03110 Example 4 or 5

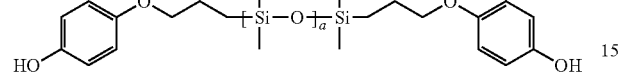

synthesized from allylphenole and Si—H terminated silicon oil, available from Shin Etsu Chemical Co., Ltd (Shih et al., J. Polym. Sci. 75 (2000) 545)

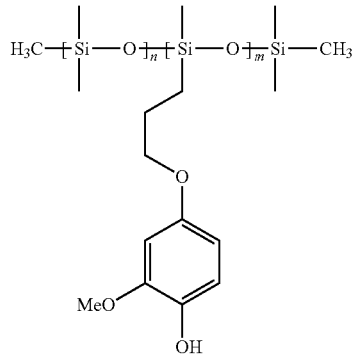

synthesized from eugenole and Si—H pendant silicon oil e.g. according to WO 97/03110. Example 1, 2 or 3

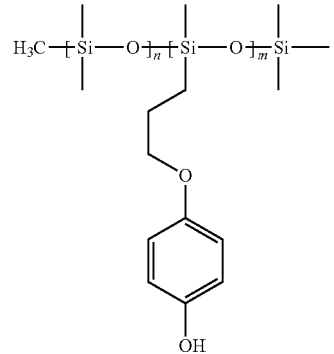

synthesized from allylphenole and Si—H pendant silicon oil

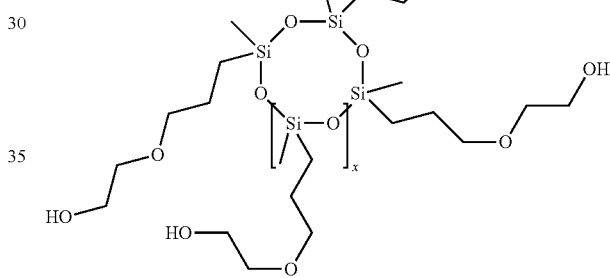

x: 4,5,6 synthesized from Si—H cyclics and allylglycol

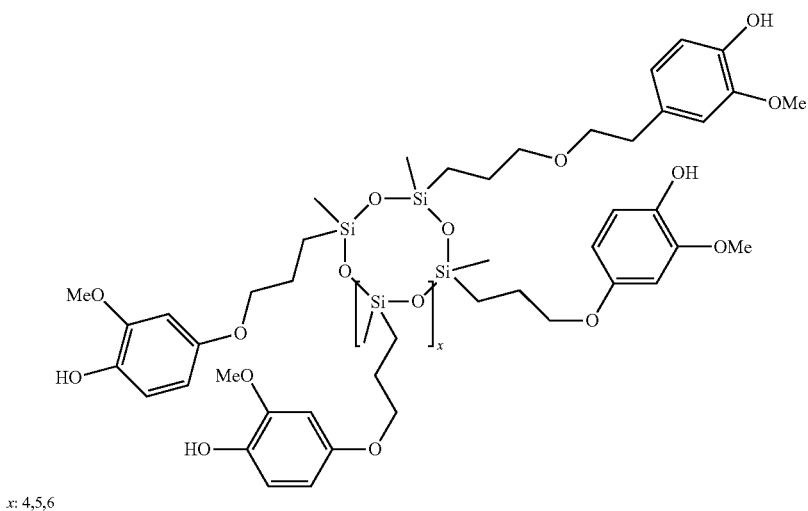

x: 4,5,6 synthesized from Si—H cyclics and eugenole.

Especially preferred are also silicone oils with pendant carbinol groups like e.g. Silwet L-7200, L-7210, L-7220, L7230, L-7604, L-7644 or L-7657 of OSi Company.

Component B is typically present in the following amounts:
Lower limit: at least 6 wt. %;
Upper limit: utmost 20 or utmost 18 or utmost 15 wt. %;
Range: from 6 to 20 or from 6 to 18 or from 6 to 15 wt. %;
wt. % with respect to the weight of the whole composition.

The curable composition also comprises a filler system.

Either of the pastes or compositions described in the present text may contain filler(s) as component D, in particular an inorganic filler.

The chemical nature and structure of the filler(s) is not particularly limited unless it is contra productive for achieving the intended result.

According to one embodiment, the paste(s) described in the present text comprise reinforcing filler(s) as component D1.

The filler D1 may be described by the following feature: having a BET surface of at least 50 $m^2/g$, e.g. from 50 to 400 $m^2/g$. If desired, the BET surface of the filler can be determined as described in DIN 66132.

Suitable filler(s) D1 include pyrogenic or fumed or precipitated silicic acid. Those filler are commercially available from companies like Wacker or Degussa under the trade names Aerosil™, Sipernat™, HDK-H™ or Aeroxide™.

The surface of the filler D1 may be surface treated, e.g. by treatment with organosilanes or siloxanes or by the etherification of hydroxyl groups to alkoxy groups. The surface treatment can be carried out, e.g. with dimethyldichlorosilane, hexamethyl-di silazane, tetramethylcyclotetrasiloxane or polymethylsiloxane.

If present, filler D1 may be present in the following amounts:
Lower amount: at least 0.1 or at least 0.5 or at least 1 wt. %;
Upper amount: utmost 20 or utmost 15 or utmost 10 wt. %;
Range: from 0.1 to 20 or from 0.5 to 15 or from 1 to 10 wt. %;
wt-% with respect to the weight of the respective Part I or Part II.

If the amount of the filler D1 is too high, the consistency and rheological properties of the pastes will not be adequate for an impression material to capture good detail accuracy of the preparation margins and teeth in a patient's mouth.

If the amount of the filler D1 is too low, the strengthening effect maybe too low and separation effects in the paste may occur, e.g. sedimentation of fillers.

According to one embodiment, the paste(s) described in the present text comprise non-reinforcing filler(s) as component D2.

Inorganic filler D2 may be described by the following features:
maximum particles size: 200 μm or below; or 150 μm or below;
BET surface: below 50 $m^2/g$; or from 1 to 40 $m^2/g$.

Examples for the inorganic filler component D2 include quartz, cristobalite, calcium silicate, diatomaceous earth, zirconium silicate, montmorillonite such as bentonite, zeolite, including molecular sieves such as sodium aluminium silicate, metal oxide powder such as aluminium oxide, titanium oxide or zinc oxide or their mixed oxides, barium sulphate, calcium carbonate, plaster, glass and mixtures thereof.

If desired, the inorganic filler component D2 can be surface-treated, as well. The surface treatment can generally be carried out with the same methods as described in the case of inorganic filler component D1.

If present, filler D2 may be present in the following amounts:
Lower amount: at least 0.1 or at least 1 or at least 10 wt. %;
Upper amount: utmost 70 or utmost 60 or utmost 50 wt. %;
Range: from 0.1 to 70 or from 1 to 60 or from 10 to 50 wt. %;
wt. % with respect to the weight of either Part I or Part II.

If the amount of filler D2 is too high, hardness of the set impression will become too high so that it can become difficult to remove it from a patient's mouth.

If the amount of the filler D2 is too low, the required hardness of the set impression to be able to pour it with gypsum without distortions may not be achieved.

Using a combination of reinforcing filler D1 and non-reinforcing fillers D2 can sometimes be preferred.

In this respect, the quantity of reinforcing fillers D1 can range from 0.1 to 10 wt. %, in particular from 0.4 to 8 wt. % with respect to the respective Catalyst Part I or Base Part II.

The total amount of filler is typically within a range from 0.1 to 70 wt. % or from 1 to 60 wt.-% or from 10 to 50 wt. %.

The curable composition also comprises a catalyst system.

The catalyst system comprises two kind of catalysts:
an addition cure catalyst component C-A suitable to cure components A1 and A2, and
a condensation catalyst component C-B suitable to cure component B.

The catalyst component C-A functions as an addition-cure catalyst.

The nature and structure of component C-A is not particularly limited unless the desired result cannot be achieved.

The addition cure catalyst is typically a platinum catalyst or a platinum containing catalyst, including a platinum complex which can be prepared from hexachloroplatinum acid by reduction with tetramethyldivinyldisiloxane. Such compounds are known to the skilled person.

Any other compounds which catalyze or accelerate addition cross-linking of silanes with ethylenically unsaturated double bonds are also suitable. Platinum-siloxane complexes as described, e.g. in U.S. Pat. Nos. 3,715,334, 3,775, 352 and 3,814,730 are suitable. The disclosure of these patents with regard to platinum complexes and their preparation is explicitly mentioned and expressly regarded as part of the disclosure of the present text.

If the catalyst is a Pt containing catalyst, the catalyst component C-A may be present in the following amounts:
Lower amount: at least 0.00005 or at least 0.0002 wt. %;
Upper amount: utmost 0.05 or utmost 0.04 wt. %;
Range: from 0.00005 to 0.05 or from 0.0002 to 0.04 wt. %,
calculated as elemental platinum and related to the weight of the whole composition.

The nature and structure of the condensation cure catalyst component C-B is not particularly limited unless the desired result cannot be achieved.

Examples of condensation cure catalyst component C-B include aluminum alkoxides, antimony alkoxides, barium alkoxides, boron alkoxides, calcium alkoxides, cerium alkoxides, erbium alkoxides, gallium alkoxides, silicon alkoxides, germanium alkoxides, hafnium alkoxides, indium alkoxides, iron alkoxides, lanthanum alkoxides, magnesium alkoxides, neodymium alkoxides, samarium alkoxides, strontium alkoxides, tantalum alkoxides, titanium alkoxides, tin alkoxides, vanadium alkoxide oxides, yttrium alkoxides, zinc alkoxides, zirconium alkoxides, titanium or zirconium compounds, especially titanium and zirconium alkoxides, and chelates and oligo- and polycondensates of the above alkoxides, dialkyltin diacetate, tin(II)octoate, dialkyltin diacylate, dialkyltin oxide and double metal alkoxides. Double metal alkoxides are alkoxides containing two different metals in a particular ratio. In particular, the following are employed: titanium tetraethylate, titanium tetrapropylate, titanium tetraisopropylate, titanium tetrabutylate, titanium tetraisooctylate, titanium isopropylate tristearoylate, titanium triisopropylate stearoylate, titanium diisopropylate distearoylate, zirconium tetrapropylate, zirconium tetraisopropylate, zirconium tetrabutylate. In addition, titanates, zirconates and hafnates as described in DE 4427528 C2 and EP 0 639 622 B1 can be used.

According to one embodiment, catalyst component C-B can be characterized by one or more of the following features:
being present in an amount from 0.1 to 15 wt. % with respect to the weight of the whole composition;
comprising a Ti, Zr, Zn or Sn containing component.

The curable composition may optionally comprise one or more surfactant(s) as component E.

Surfactants or hydrophilizing agents which can be employed can generally be chosen freely from all types of surfactants which improve the hydrophilicity of a silicone moiety containing material (especially, if curable via a hydrosilylation reaction).

Useful surfactants can generally be chosen from anionic, cationic or non-ionic surfactants or mixtures of two or more of such types of surfactants.

It can be preferred, if the hardenable composition comprises a non-ionic surfactant as a hydrophilizing agent or a mixture of two or more non-ionic surfactants.

Ethoxylated fatty alcohols can be used. Suitable examples are e.g. described in EP 0 480 238 B1.

Also preferred are non-ionic surface-active substances including nonylphenolethoxylates, polyethylene glycolmono- and diesters, sorbitan esters and polyethylene glycolmono- and diethers. Suitable examples are described e.g. in U.S. Pat. No. 4,782,101. The content of these documents with regard to hydrophilizing agents and their preparation is herewith incorporated by reference.

Suitable hydrophilizing agents also include wetting agents from the group of hydrophilic silicone oils, which are not capable of being covalently incorporated into the hardened polymer network. Suitable hydrophilizing agents are described e.g. in U.S. Pat. No. 4,657,959 and in EP 0 231 420 B1. The content of these documents with regard to hydrophilizing agents and their preparation is herewith incorporated by reference.

Suitable silicone moieties containing surfactants can be summarized under the following formula:

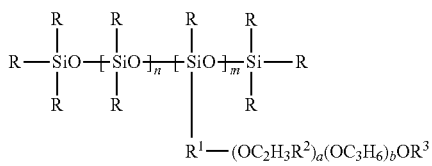

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is about zero or about one, m is about one to about five, a is about five to about 20 and b is about 0.

Several of such ethoxylated surfactants are for example available from Momentive Performance Materials Inc. including "Silwet™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL™ SF19, as obtainable from Lubrizol performance products, Spartanburg, US.

Useful surfactants also include polyether carbosilanes of the general formula Q-P—$(OC_nH_{2n})_x$—OT, in which Q stands for $R_3$—Si— or $R_3$—Si—$(R'$—$SiR_2)_a$—$R'$—$SiR''_2$—
where every R in the molecule can be the same or different and stands for an aliphatic $C_1$-$C_{18}$, a cycloaliphatic C6-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or $R_3SiR'$ in the case of a=0, and a=0-2; P stands for a $C_2$-$C_{18}$ alkylene group, preferably a $C_2$-$C_{14}$ alkylene group or A-R''', where A represents a $C_2$-$C_{18}$ alkylene group and R''' a functional group from the following list: —NHC(O)—, —NHC(O)—$(CH_2)_{n-1}$—, —NHC(O)C(O)—, —NHC(O)$(CH_2)_vC(O)$—, —OC(O)—, —OC(O)—$(CH_2)_{n-1}$—, —OC(O)C(O)—, —OC(O)$(CH_2)_vC(O)$—, —$OCH_2CH(OH)CH_2OC(O)$$(CH_2)_{n-1}$—, —$OCH_2CH(OH)CH_2OC(O)(CH_2)_vC(O)$— with v=1-12; T is H or stands for a $C_1$-$C_4$ alkyl radical or a $C_1$-$C_4$ acyl radical; x stands for a number from 1 to 200 and n stands for an average number from 1 to 6, preferably 1 to 4. Thus, the element —$SiR''_2$— can also comprise the substructure —$Si(R)(R_3SiR')$—.

The polyether part can be a homopolymer, but can also be a statistical, alternating or block copolymer.

Suitable polyether carbosilanes are selected from the group consisting of:
$Et_3Si$—$(CH_2)_3$—O—$(C_2H_4O)$y-$CH_3$, Et=Ethyl; $Et_3Si$—$CH_2$—$CH_2O$—$(C_2H_4O)$y-$CH_3$, Et=Ethyl; $(Me_3Si$—$CH_2)_3Si$—$(CH_2)_3$—O—$(C_2H_4O)$y-$CH_3$, Me=Methyl; $Me_3Si$—$CH_2$—$SiMe_2$-$(CH_2)_3$—O—$(C_2H_4O)$y-$CH_3$, Me=Methyl; $(Me_3Si$—$CH_2)_2SiMe$-$(CH_2)_3$—O—$(C_2H_4O)$y-$CH_3$, Me=Methyl; $Me_3Si$—$(CH_2)_3$—O—$(C_2H_4O)$y-$CH_3$, Me=Methyl; $Me_3Si$—$CH_2CH_2$—O—$(C_2H_4O)$y-$CH_3$, Me=Methyl; $Ph_3Si$—$(CH_2)_3$—O—$(C_2H_4O)$y-$CH_3$, Ph=phenyl; $Ph_3Si$—$CH_2$—$CH_2$—O—$(C_2H_4O)$y-$CH_3$, Ph=phenyl; $Cy_3Si$—$(CH_2)_3$—O—$(C_2H_4O)$y-$CH_3$, Cy=cyclohexyl; $Cy_3Si$—$CH_2CH_2$—O—$(C_2H_4O)$y-$CH_3$, Cy=cyclohexyl; $(C_6H_{13})_3Si$—$(CH_2)_3$—O—$(C_2H_4O)$y-$CH_3$, $(C_6H_{13})_3Si$—$CH_2CH_2$—O—$(C_4H_4O)$y-$CH_3$ in which y conforms to the relation: 5≤y≤20 and mixtures thereof.

Surfactants which can also be used, either alone or as a mixture of two or more thereof, can be found in U.S. Pat. No. 5,750,589 (Zech et al), col. 2, l. 47 to col. 3 l. 27 and col. 3, l. 49 to col. 4, l. 4 and col. 5, l. 7 to col. 14, l. 20.

Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.) p 4, l. 1 to p. 5, l. 16 and in the examples.

The content of these documents with regard to hydrophilizing agents and their preparation is herewith incorporated by reference.

In a particular embodiment, a mixture of a silicone moieties containing surfactant and one or more non-ionic surfactants selected from alkoxylated hydrocarbon surfactants is used.

Examples of useful non-ionic surfactants include those according to the formula:

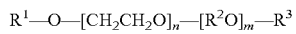

wherein $R^1$ represents an aromatic or aliphatic, linear or branched hydrocarbon group having at least 8 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which $R^1$ in the above formula represents an alkyl group of 4 to 20 carbon atoms, m is 0 and $R^3$ is hydrogen. An example thereof includes isotridecanol ethoxylated with about 8 ethoxy groups and which is commercially available as GENAPOL® X080 from Clariant GmbH. Non-ionic surfactants according to the above formula in which the hydrophilic part comprises a block-copolymer of ethoxy groups and propoxy groups may be used as well. Such non-ionic surfactants are commercially available from Clariant GmbH under the trade designation GENAPOL® PF 40 and GENAPOL® PF 80. Further suitable non-ionic surfactants that are commercially available include Tergitol™ TMN 6, Tergitol™ TMN 10, or Tergitol™ TMN 100x. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

Besides or in addition to the hydrophilazing agent(s) described above, the composition may comprise any of the following components:
ethylene oxide or propylene oxide polymers or ethylene-propylene block polymers bearing as end groups polymerizable moieties selected from vinly, allyl, —OCO—(CH$_3$)C=CH$_2$;
H$_3$C—CO—[CH$_2$—CH$_2$—O—]$_m$—[CH$_2$—CH$_2$—CH$_2$—O—]$_n$—CO—CH$_3$ with n,m=10 to 100.

In addition to the hydrophilazing agent(s) mentioned above, the composition may also comprise one or more F-containing component as hydrophilating agent.

Suitable examples of the F-containing compound include:

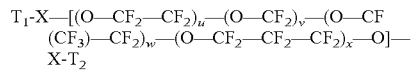

with u=0 to 8, v=0 to 8, w=0 to 14 and x=0 to 8 and u+v+w+x≥1, wherein T$_1$ and T$_2$ can be equal or different and are independently selected from the group consisting of —COOR, —CONR$^b$R$^c$—CH$_2$OH, —CF$_2$OR, —CHFOH, —CHFOR, —CH$_2$OR or —F with R and being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R, and wherein X is selected from (CF$_2$)$_{1\text{-}6}$, CF(CF$_3$) and CHF—CF$_2$.

More precisely, the F-containing component can also be characterized by any of the following formulas:
Rf-(O)$_t$—CHF—(CF$_2$)$_x$-T, with t=0 or 1, x=0 or 1 and Rf being a linear or branched per- or partly fluorinated alkyl rest (including C1 to C6 or C1 to C4), wherein the alkyl chain can be interrupted by O atoms, with the proviso that when t is 0, the Rf group is a linear or branched per- or partly fluorinated alkyl rest (including C1 to C6 or C1 to C4) interrupted by one or more O atoms,
Rf-(OCF$_2$)$_m$—O—CF$_2$-T, with m=1 to about 6 and Rf being a linear or branched per- or partly fluorinated alkyl rest (including C1 to C6 or C1 to C4), wherein the alkyl chain can be interrupted by O atoms,
CF$_3$—(CF$_2$)$_2$—(OCF(CF$_3$)—CF$_2$)$_z$—O-L-T, with z=0, 1, 2, 3, 4, 5, 6, 7 or 8, L having a structure selected from —CF(CF$_3$)—, —CF$_2$—, —CF$_2$CF$_2$— and —CHFCF$_2$,
Rf-(O—CF$_2$CF$_2$)$_n$—O—CF$_2$-T, with n=1, 2, 3, 4 or 5 and Rf being a linear or branched per- or partly fluorinated alkyl rest (including C1 to C6 or C1 to C4), wherein the alkyl chain can be interrupted by O atoms,
an oligomeric compound obtainable by the anionic or photochemical (in the presence of oxygen) polymerization or copolymerisation of monomers selected from vinylidenfluoride, hexafluoropropylenoxide, tetrafluoroethylene, 2,2,3,3-tetrafluorooxetane, trifluoroethylene or monofluoroethylene, wherein at least one chain-end of the oligomeric compound is represented by a function T,
T being selected from the group consisting of —COOR, —CONR$^b$R$^c$—CH$_2$OH, —CF$_2$OR, —CHFOH, —CHFOR, —CH$_2$OR or —F with R and being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R.

Specific examples of T include:
a) homo- or copolymerization of hexafluoropropylenoxide and/or 2,2,3,3-tetrafluorooxetane;
b) homo- or copolymerization of vinylidenfluoride, hexafluoropropylenoxide, tetrafluoroethylene, 2,2,3,3-tetrafluorooxetane, trifluoroethylene and/or monofluoroethylene in the presence of oxygen In particular, the esters, especially the methylesters, and the amidols (T=C(O)NH— alkyl-OH) and the respective alcohols or methylethers, prepared by chemical reduction, of the following structures can be used.

Further examples can be found in EP 2 231 102 B1. The content of this reference with respect to the description of F-containing components is herewith incorporated by reference.

The F-containing components described above typically function as wetting-enabler, that is, they do not show hydrophiliating properties if used alone (i.e. without an additional surfactant), but increase the hydrophilating properties of an additionally added surfactant.

Particularly useful are hexafluoropropylene oxide (HFPO) derivatives including carboxyl ester derivatives and amidol derivatives of HFPO.

HFPO can be obtained as described in U.S. Pat. No. 3,242,218 or US 2004/0124396. The general formula of a methyl ester derivative of HFPO is $C_3F_7O[CF(CF_3)CF_2O]_nCF(CF_3)COOCH_3$ with n being 2 to 14.

If present, the surfactant(s) are present in the following amounts:
Lower amount: at least 0.05 or at least 0.1 or at least 0.5 wt. %;
Upper amount: utmost 10 or utmost 8 or utmost 5 wt. %;
Range: from 0.05 to 10 or from 0.1 to 8 or from 0.5 to 5 wt. %;
with respect to the weight of the whole composition.

The curable composition may optionally comprise one or more additive(s) as component F.

The chemical nature and structure of the additive(s) is not particularly limited unless it is contra productive for achieving the intended result.

Additive(s) which might be present include retarder(s), inhibitor(s), colourant(s), stabilizer(s), flavouring(s), hydrogen scavenger(s), rheology modifier(s), astringent(s), compatibilizer(s) and mixtures thereof.

To control the reactivity of the addition reaction and to prevent premature curing, it may be advantageous to add an inhibitor, which prevents the addition reaction for a specific period of time or slows the addition reaction down. Such inhibitors are known and described, e.g. in U.S. Pat. No. 3,933,880. This content of this reference regarding such inhibitors and their preparation is expressly regarded as being part of the disclosure of the invention and herewith incorporated by reference.

Examples of such inhibitors include acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based on vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups.

The paste(s) may also contain a component useful for diminishing the presence or degree of hydrogen outgassing which may be typically generated as a result of the vinyl polymerization in the case of SiH curable composition.

The composition thus may comprise a hydrogen scavenger such as finely divided platinum metal that scavenges for and takes up such hydrogen. The Pt metal may be deposited upon a substantially insoluble salt having a surface area of between about 0.1 and about 40 m$^2$/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal (e.g. as described e.g. in U.S. Pat. No. 4,273,902) or Pd compounds (e.g. as disclosed in to U.S. Pat. No. 5,684,060) can be employed.

The paste(s) may further contain a stabilizer as component, e.g. selected from antioxidants and mixtures thereof.

Useful antioxidant(s) which can be used include: Vitamin E; N,N'-di-2-butyl-1,4-phenylenediamine; N,N'-di-2-butyl-1,4-phenylenediamine; 2,6-di-tert-butyl-4-methylphenol; 2,4-dimethyl-6-tert-butylphenol; 2,4-dimethyl-6-tert-butylphenol and 2,6-di-tert-butyl-4-methylphenol; 2,6-di-tert-butylphenol; Pentaerythritoltetrakis(3-(3,5-di-tert-butyl-4-hydroxyphenyl)propionate) (Irganox™ 1010); Octyl-3,5-di-tert-butyl-4-hydroxy-hydrocinnamate; Octadecyl 3-(3,5-di-tert-butyl-4-hydroxyphenyl)propionate; 1,3,5-Trimethyl-2,4,6-tris(3,5-di-tert-butyl-4-hydroxybenzyl)benzene; 2,2,4,4-Tetrakis-tert-butyl-3,3-dihydroxybiphenyl; 4,4-Butylidenebis(6-tert-butyl-m-cresol); 4,4'-Isopropyliden-bis-(2-tert-butylphenol); 2,2'-methylenebis(6-nonyl-p-cresol); 1,3,5-tris(3,5-di-tert-butyl-4-hydroxybenzyl-)—1,3,5-triazine-2,4,6(1H,3H,5H)trione; or mixtures thereof. Particularly useful include antioxidants comprising a phenolic moiety, especially a sterically hindered phenolic moiety.

Other stabilizers which can be used include stabilizers containing a phosphorous moiety, like organo phosphines, organo-phosphites, organo-phosphonites, di(organo-phoshites, di(organo-phosphonites) and mixtures thereof. A more detailed description of those stabilizers is given on page 16, line 30 to page 18, line 15 of WO 2007/001869 A2. The content of WO 2007/001869 with respect to these stabilizers is herewith incorporated by reference.

Astringent(s) which may be present include aluminium salts like aluminium sulfate, aluminium ammonium sulfated, aluminium chlorohydrated, aluminium acetate and mixtures thereof. Useful astringent(s) can also contain iron, manganese and/or zinc containing substances.

The paste(s) may comprise a flavorant or mixtures of flavorants to improve the taste and/or smell of the composition. Flavorants, which can be used, include isoamylacetate (banana), benzaldehyde (bitter almond), cinnamic aldehyde (Cinnamon), ethylpropionate (fruity), methyl anthranilate (Grape), mints (e.g. peppermints), limonene (e.g. Orange), Allylhexanoate (pineapple), ethylmaltol (candy), ethylvanillin (Vanilla), methylsalicylate (Wintergreen).

Examples of colorants which can be used include chinoline yellow dye (sicovit), chromophthalblue A3R, red iron oxide 3395, Bayferrox 920 Z Yellow, Neazopon Blue 807 (copper phthalocyanine-based dye), Helio Fast Yellow ER, Brilliant Blue FCF, Fast Green FCF and/or Orange Yellow S. Pigments or dyes which are stable under acidic conditions are preferred.

Suitable compatibilizer(s) include silicone components with an aliphatic (e.g. $C_8$ to $C_{20}$) side chain.

The use of colorants is sometimes preferred, as it may facilitate the visibility of the composition in the mouth of the patient, in particular, if the composition is used for dental retraction purposes.

If present, the additive component(s) may be present in the following amounts:
Lower amount: at least 0.01 or at least 0.1 wt. %;
Upper amount: utmost 20 or utmost 15 wt. %;
Range: from 0.01 to 20 or from 0.1 to 15 wt. %
wt. % with respect to the weight of the whole composition.

The curable composition is provided as a kit of parts. The kit of parts comprises a Catalyst Part or Paste I and a Base Part or Paste II.

The Catalyst Part comprises components C-A, C-B and A1.

The Base Part comprises components A2, A1 and B.

The other components D, E and F can be present either in the Catalyst Part or the Base Part or the Catalyst Part and the Base Part.

Thus, the curable composition described in the present text is provided in form of a catalyst part and a base part, wherein the two parts are to be combined shortly before use to avoid a premature hardening or curing during storage.

The Catalyst Part I and the Base Part II are typically provided in a ratio from 1:1 to 1:10 or from 1:1 to 1:5 or from 1:1 to 1:4 by volume. Thus, according to one embodiment the Base Part II is present in excess compared to the Catalyst Part I.

According to one embodiment, the composition described in the present text comprises the components in the following amounts:

polyorganosiloxane with at least two olefinically unsaturated groups as component A1 from 0.1 to 45 or from 1 to 40 or from 3 to 35 wt., organohydrogenpolysiloxane as component A2 from 0.1 to 20 or from 1 to 15 wt. %, vinyl functional QM silicone component as component A3 from 0.1 to 65 or from 1 to 60 or from 3 to 55 wt. %, alkylsiloxane having at least one carbinol, silanol, or alkoxy as component B of 6 wt. % or more, filler system as component D from 0.1 to 70 or from 1 to 60 or from 10 to 50 wt. %, surfactant(s) as component E from 0.05 to 10 or from 0.1 to 8 or from 0.5 to 5 wt. %, additive(s) as component from 0.01 to 20 or from 0.1 to 15 wt. %, catalyst component C-A from 0.00005 to 0.05 or from 0.0002 to 0.04 wt. %, catalyst component C-B from 0.1 to 15 wt. % wt. % with respect to the weight of the whole composition.

The compositions of the Catalyst Part and the Base Part of the curable composition described in the present text can be produced by mixing the individual components contained in the respective paste(s), e.g. by using a speed-mixer or kneader.

The compositions of the Catalyst Part and the Base Part of the curable composition described in the present text are typically stored until use in a suitable packaging device. Suitable packaging devices include syringes, foil bags, tubes or cartridges.

These packaging devices are either inserted into a manually or electrically driven dispensing device (e.g. if a foil bag or cartridge is used) or function as delivery or dispensing system on its own (e.g. if a syringe is used).

To enable an adequate mixing of the respective compositions, the packaging devices are typically equipped with a static or dynamic mixer.

Thus, the invention is also directed to a system for storing and delivering the composition as described in the present text.

The composition described in the present text is useful as dental retraction material.

A dental retraction material is typically applied in a process comprising the steps of:
mixing the compositions of the Catalyst Part and the Base Part of the curable composition,
applying the obtained mixture into the sulcus of a tooth (e.g. in an amount of 5 to 500 µl per tooth),
letting the composition cure,
removing the cured composition from the sulcus.

The invention relates also to a kit of parts comprising the curable composition as described in the present text with either of the following components alone or in combination:
Dental impression material;
Retraction caps;
Application device;
Impression Trays.

According to a further embodiment, the curable composition described in the present text does typically not comprise either of the following components alone or in combination:
Alkylsiloxane(s) having at least one amino group in an amount of more than 1 wt. %;
Water in an amount of more than 1 wt. %;
wt. % with respect to the weight of the whole composition.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized water, and all molecular weights are weight average molecular weight.

Moreover, unless otherwise indicated all experiments were conducted at ambient conditions (23° C.; 1013 mbar).
Methods
Shore Hardness A If desired, the Shore hardness can be determined according to DIN ISO 7619-1:2012-02.
Consistency The consistency of pastes to be mixed is determined according to DIN EN ISO 4823:2015-12. If the consistency is to be determined for a single paste, the same procedure is applied, however, leaving out the steps of mixing the pastes and waiting at least 15 min for the material to fully cure before measuring the diameter of the composition under a predefined load.
Residual Gap Behavior The capability of a curable paste to open a sulcus and to keep a sulcus open during setting time of the paste can be determined by a device using a stamp which creates pressure created by a spring onto the curable paste in a small slit (residual gap device).

More precisely, the method can be described as follows: The gap resistance can be determined as follows:

A mold having a rectangular shape with the dimensions: x (depth)=7.5 mm, y (width)=18.0 mm and z (height)=12.0 mm is provided.

The mold (1) is formed by three immovable sidewalls (1a), (1b), (1c) and one movable sidewall (1d), all located on a plane surface (2). The movable sidewall (1d) is equipped with a spring (3) having a defined spring pressure of 20N. The spring is compressed and fixed by a removable fixation means (4). The moveable sidewall (1d) is adjusted to a pre-defined depth of 7.5 mm (x-direction). A device for determining the consistency is shown in FIG. 1. The mold is filled with the curable composition.

After a pre-defined time T1, the fixation means (4) of the spring (3) is removed having the result that the spring (3) exerts a predefined pressure on the curable composition through the movable sidewall (1d). A portion of the curable composition is pressed out of the mold (1). The depth of the mold is decreasing which can be determined by measuring the distance for x (mm) using e.g. a length gauge (5). After a pre-defined time T2, the value for x (mm) is determined.

The higher the value x at time T2 is, the higher the consistency/residual gap behavior of the composition is.

For all results reported below, T1=60 s from start of mixing; T2=70 s from start of mixing.

For the invention described in the present text, for retraction pastes a value of ≥2.0 mm is considered to be sufficient to provide enough resistance to keep a sulcus in the mouth open.

This method is also described by P. Osswald, J. Zech, H. Hoffmann, A. Syrek, D. Krueger in Abstract 1124, AADR 2016, Los Angeles USA ("Retraction Capability of Different Types of Materials").

Tensile Strength and Elongation at Break

If desired, the tensile strength and elongation of the compositions can be determined according to DIN53504. The tensile strength is given in MPa and the elongation in % of the original length. Tensile strength and elongation data were evaluated by tearing six I-shaped specimens with a central unit of 20 mm×4 mm×2 mm in a Zwick Z020 Universal testing machine. Base and catalyst pastes are mixed using a spatula in the given weight ratio and filled into a brass mound. After 3 h at 23° C. the specimen are removed, three measurements are made and the mean value determined (speed 200 mm/min).

Viscosity

If desired, the viscosity of raw materials (except for pastes) can be measured at 23° C. using a ThermoHaake Rotovisco 1 device with a plate/plate system (diameter 20 mm) and a slit of 0.2 mm. The viscosity values (Pas) and share stress values (Pa) can be recorded for each share rate (starting from 10 l/s to 100 l/s in 10 l/s steps. For each share rate, a delay of 5 seconds was used before collecting data. The above mentioned method of measurement corresponds essentially to DIN 53018-1.

Water Contact Angle

If desired, the water contact angle of the uncured paste can be measured as follows: Test specimen preparation: For the preparation of test piece the mixed paste is subjected to an object slide and flattened and triturated by a second object slide in order to obtain a thin film. The test piece preparation is performed in that simplified way as the thickness of the film does not have a significant effect on the measured water contact angle (see G. Kugel, T. Klettke, J. A. Goldberg, J. Benchimol, R. D. Perry, S. Sharma, J. Prosthod. 2007, 16, 84-92). Measurement: The object slide is placed on the table of a Drop Shape Analyze System DSA 10 (Kruss GmbH, Hamburg), a well-known device for measuring contact angles. 5 µl of water are placed onto the surface of the specimen and an automatic contact angle measurement is started using standard software of the goniometer. Measuring time is at least about 10 s up to about 200 s. The water contact angle is measured at different time periods after mixing of base paste and catalyst paste, especially after 25 s. The data (video sequences) is evaluated by the "circle fitting" method, another standard method for data evaluation (see G. Kugel, T. Klettke, J. A. Goldberg, J. Benchimol, R. D. Perry, S. Sharma, J. Prosthod. 2007, 16, 84-92); Θ 2 s is the angle obtained 2 s after placing the water drop on the surface.

Mixability in a Static Mixing Tip for Retraction Purposes

The mixability in a static mixer is determined by filling the sample pastes into a 3M intra-oral syringe green with a mixing ratio of 1:1, or purple with a mixing ratio of 2:1 (depending on the desired mixing ratio—3M Intra-oral syringes green or purple available from 3M—Order code 71507 res. 71505). The intra-oral tip is cut off the mixing cannula and is replaced by an empty 3M Retraction capsule. The ease of the extrusion of the pastes through the applicator is rated by the operator on the scale of ++/+/~/--.

Optionally the extrusion forces can also be tested by inserting the applicator in an Universal material testing machine (e.g. Zwick Z020).

Materials

| Name | Description |
| --- | --- |
| Polymer 1 | Vinyl-terminated Polydimethylsiloxane; 10,000 mPa*s |
| Polymer 2 | Vinyl-terminated Polydimethylsiloxane; 2,000 mPa*s |
| Polymer 3 | Vinyl-terminated Polydimethylsiloxane; 200 mPa*s |
| Polymer 4 | Polydimethylsiloxane dicarbinol terminated; 3,200 mPa*s |
| Polymer 5 | Vinyl-terminated Polydimethylsiloxane; 1,000 mPa*s |
| VQM-Resin 1 | QM-Resin compound containing Vinyl groups; 0.20 mmol/g Vinyl, 10,000 mPa*s |
| VQM-Resin 2 | QM-Resin compound containing Vinyl groups; 0.23 mmol/g Vinyl, 1,300 mPa*s |
| Crosslinker 1 | Organohydrogenpolysiloxane (SiH: 1.9 mmol/g) |
| Crosslinker 2 | Organohydrogenpolysiloxane (SiH: 3.8 mmol/g) |
| Crosslinker 3 | Organohydrogenpolysiloxane (0.16% H2) |
| Filler 1 | Cristobalit flour d90 = 9 µm |
| Filler 2 | Hydrophobic fumed silica (BET 80-120 m$^2$/g) |
| Filler 3 | Silane treated Cristobalite filler d90 = 9 µm |
| Filler 4 | Calciumsilicate |
| Filler 5 | Zeolit |
| Additive 1 | Stabilizer - Hostanox ™ P-EPQ |
| Additive 2 | Antioxidant - Irganox ™ 1010 |
| Additive 3 | Ethoxylated Surfactant |
| Additive 4 | Tetraallylsilane |
| Plasticizer 1 | Mineral oil |
| Plasticizer 2 | Vaseline |
| Pigment | Blue pigment |
| Addition cure catalyst | Platinum tetramethyldivinyldisiloxane complex; 1.3 wt.-% Pt in silicone oil containing in addition 2.875 wt.-% of Divinyltetramethyldisloxane |
| Condensation cure catalyst | Titanium isopropoxide (>98%) |
| Retarder | Divinyltetramethyldisloxane |

General Description of Preparation

All Examples are prepared by homogenizing the respective components to a uniform paste using a planetary mixer with vacuum capabilities (Speedmixer DAC 600.1 VAC-P).

Formulations:

|  | Ex. A | Ex. B | Comp. Ex. C | Comp. Ex. D |
|---|---|---|---|---|
| Base Part | | | | |
| Polymer 1 | 24.00 | | | |
| Polymer 2 | | | | 15.0 |
| Polymer 3 | 9.75 | | | 12.0 |
| Polymer 4 | 12.0 | 18.0 | 10.0 | 4.0 |
| VQM-Resin 1 | | 39.5 | 47.5 | |
| VQM-Resin 2 | | | | |
| Crosslinker 1 | 5.5 | 6.0 | 6.0 | |
| Crosslinker 2 | 6.0 | 5.0 | 5.0 | |
| Crosslinker 3 | | | | 4.5 |
| Filler 1 | 35.5 | 25.5 | 25.5 | 52.4 |
| Filler 2 | 3.5 | 3.0 | 3.0 | |
| Filler 4 | | | | 12.0 |
| Filler 5 | | 1.0 | 1.0 | |
| Pigment | | | | 0.1 |
| Additive 1 | 0.012 | 0.008 | 0.008 | |
| Additive 2 | 0.012 | 0.008 | 0.008 | |
| Additive 3 | 2.976 | 1.984 | 1.984 | |
| Additive 4 | 0.75 | | | |
| Catalyst Part | | | | |
| Plasticizer 1 | 10.0 | | | 16.42 |
| Plasticizer 2 | 16.95 | | | 15.92 |
| Polymer 3 | 10.5 | | | |
| Polymer 5 | | 6.0 | 6.0 | |
| VQM-Resin 1 | | 43.0 | 43.0 | |
| VQM-Resin 2 | | | | |
| Filler 2 | 4.0 | 3.0 | 3.0 | 4.49 |
| Filler 3 | 50.9 | 42.9 | 42.9 | 56.58 |
| Filler 5 | 2.0 | 2.0 | 2.0 | |
| Pigment | 0.10 | 0.1 | 0.1 | 0.1 |
| Addition cure catalyst | 2.5 | 1.5 | 1.5 | 1.5 |
| Condensation cure catalyst | 2.5 | 1.5 | 1.5 | 4.99 |
| Retarder | 0.05 | | | |
| Additive 4 | 0.50 | | | |

The compositions were tested with respect to mixability and residual gap resistance.

|  | Ex. A | Ex. B | Comp. Ex. C | Comp. Ex. D |
|---|---|---|---|---|
| Mixing Ratio (Base/Catalyst) | 2:1 | 1:1 | 1:1 | 2:1 |
| mixable in a static mixer | ++ | + | + | -- |
| Mixing Ratio (Base/Catalyst) | 2:1 | 1:1 | 1:1 | 5:1 |
| Residual Gap [mm] | 3.65 | 2.95 | 1.15 | 6.50 |

Finding:

It is shown that by using the formulations described in the present text a curable retraction composition can be prepared, that is mixable in an automix sulcus delivery device. At the same time, the capability of these compositions to keep the sulcus of a tooth open is ensured as demonstrated by the so-called residual gap resistance behaviour.

The invention claimed is:

1. A kit of parts comprising a Catalyst Part I and a Base Part II for providing a curable composition for dental retraction, the kit of parts comprising:
    the Catalyst Part I comprising:
        component A1: at least one polyorganosiloxane with at least two olefinically unsaturated groups, and
        a catalyst system comprising:
            an addition cure catalyst component C-A suitable to cure components A1 and A2, and
            a condensation cure catalyst component C-B suitable to cure component B;
    the Base Part II comprising:
        component A1: at least one polyorganosiloxane with at least two olefinically unsaturated groups
        component A2: at least one organohydrogenpolysiloxane,
        component B: at least one alkylsiloxane having at least one carbinol, silanol, or alkoxy moiety, wherein component B is present in an amount of at least 6 wt. % with respect to the weight of the curable composition,
        component D comprising filler(s) in a total amount of 10 to 50 wt % with respect to the weight of the curable composition, wherein the filler(s) are present in one or more of the Catalyst Part I and the Base Part II,
    wherein at least two different polyorganosiloxane with at least two olefinically unsaturated groups are present in the curable composition, the at least two polyorganosiloxane with at least two olefinically unsaturated groups differ in viscosity by a factor of at least 5, and
    wherein of the at least two different polyorganosiloxane with at least two olefinically unsaturated groups, a higher viscosity polyorganosiloxane is present in an amount relative to a lower viscosity polyorganosiloxane at a ratio of 0.9:1 to 3:1.

2. The kit of parts of claim 1, the addition cure catalyst component C-A being characterized by at least one of the following features:
    comprising a Pt containing component;
    being present in an amount from 0.00005 to 0.05 wt. % calculated as elemental platinum with respect to the weight of Catalyst Part I.

3. The kit of parts of claim 1, the addition cure catalyst component C-B being characterized by at least one of the following features:
    being present in an amount from 0.1 to 15.0 wt. % with respect to the weight of Catalyst Paste I;
    comprising a component comprising Ti, Zr, Zn or Sn.

4. The kit of parts of claim 1, component B being characterized by at least one or more of the following features:
    molecular weight: 900 to 500,000 g/mol;
    being present in an amount from 6 to 20 wt. % with respect to the composition.

5. The kit of parts of claim 1, component A1 comprising one or more compounds of the following formula:

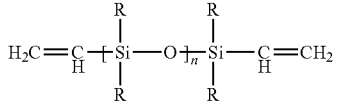

wherein each R is independently a hydrocarbon group having 1-6 carbon atoms, and
wherein n is a numerical value that provides a viscosity of component A1 between 4 and 1,000,000 mPa*s mPa*s at 23° C.

6. The kit of parts of claim 1, wherein at least one of the at least one polyorganosiloxane with at least two olefinically unsaturated groups of component A1 a vinyl functional QM silicone.

7. The kit of parts of claim 1, comprising:
polyorganosiloxane with at least two olefinically unsaturated groups as component A1 in an amount from 0.1 to 45 wt. %;
organohydrogenpolysiloxane as component A2 in an amount from 0.1 to 20 wt. %;
vinyl functional QM silicone component as component A3 in an amount from 0.1 to 65 wt. %;
alkylsiloxane having at least one carbinol, silanol, or alkoxy as component B in an amount of at least 6 wt. %;
surfactant(s) as component E in an amount from 0.05 to 10 wt. %;
additive(s) as component F in an amount from 0.01 to 20 wt. %;
catalyst component C-A in an amount from 0.00005 to 0.05 wt. %; and
catalyst component C-B in an amount from 0.1 to 15 wt. %,
wherein wt. % is with respect to the weight of the composition.

8. The kit of parts of claim 1, the curable composition being characterized by one or more of the following parameters:
curing time: within 10 min at 23° C.;
Shore hardness A: from 25 to 80 determined according to DIN ISO 7619-1:2012-02;
tensile strength: from 1.0 to 10 determined according to DIN 53504:2009-10;
consistency of Catalyst Part I and/or the Base Part II being from 25 to 50 mm determined according to ISO 4823:2015;
water contact angle of Catalyst Part I and/or the Base Part II measured 10 s after placing a drop of water onto the surface of the composition: <90°; and
residual gap resistance: at least 2.0 mm.

9. The kit of parts of claim 1, one or more of the Catalyst Part I and the Base Part II further comprising additives selected from retarder(s), inhibitor(s), colourant(s), stabilizer(s), flavouring(s), hydrogen scavenger(s), rheology modifier(s), and astringent(s), or mixtures thereof.

10. A method for retracting a tooth sulcus, the method comprising:
contacting the Catalyst Part I and the Base Part II of claim 1 to form a mixture;
applying the mixture into the tooth sulcus;
curing the mixture to form a cured composition; and
removing the cured composition from the tooth sulcus.

11. The kit of parts of claim 1, further comprising composition of one or more of the following components:
dental impression material;
retraction caps;
application device; and
impression trays.

12. The method of claim 10, wherein the applying is via a static mixing tip.

13. The kit of parts of claim 1, one or more of the Catalyst Part I and the Base Part II further comprising one or more of
component E: surfactant(s),
component F: additive(s), and
component A3: at least one vinyl functional QM silicone.

14. The kit of parts of claim 1, wherein the Catalyst Part I and the Base Part II are contained in a double-barrel syringe or double-barrel cartridge.

15. The kit of parts of claim 1, wherein at least some filler(s) of component D are reinforcing inorganic compound(s) being characterized as having a BET surface of 50 $m^2/g$ to 400 $m^2/g$.

16. The kit of parts of claim 15, wherein reinforcing inorganic compound(s) are selected from pyrogenic, fumed, precipitated, and surface-treated silicic acids, or combinations thereof.

17. The kit of parts of claim 15, wherein the reinforcing inorganic compound(s) are present in an amount from 0.1 to 20 wt. %.

18. The kit of parts of claim 1, wherein at least some filler(s) of component D are non-reinforcing inorganic compound(s) being characterized by one of more the following features:
a particle size of less than or equal to 200 μm;
a BET surface less than 50 $m^2/g$.

19. The kit of parts of claim 18, wherein the non-reinforcing inorganic compound(s) are selected from quartz, cristobalite, calcium silicate, diatomaceous earth, zirconium silicate, montmorillonite, zeolite, sodium aluminum silicate, aluminum oxide, titanium oxide, zinc oxide, barium sulphate, calcium carbonate, plaster, and glass, or combinations thereof.

20. The kit of parts of claim 18, wherein the non-reinforcing inorganic compound(s) are present in an amount from 10 to 50 wt. %.

* * * * *